US006609217B1

(12) United States Patent
Bonissone et al.

(10) Patent No.: US 6,609,217 B1
(45) Date of Patent: *Aug. 19, 2003

(54) SYSTEM AND METHOD FOR DIAGNOSING AND VALIDATING A MACHINE OVER A NETWORK USING WAVEFORM DATA

(75) Inventors: Piero Patrone Bonissone, Schenectady, NY (US); Yu-To Chen, Niskayuna, NY (US); Vipin Kewal Ramani, Niskayuna, NY (US); Rasiklal Punjalal Shah, Latham, NY (US); John Andrew Johnson, Delafield, WI (US); Phillip Edward Steen, Delafield, WI (US); Ramesh Ramchandran, Overland Park, KS (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/578,401

(22) Filed: May 26, 2000

Related U.S. Application Data

(63) Continuation-in-part of application No. 09/050,143, filed on Mar. 30, 1998, now Pat. No. 6,105,149.

(51) Int. Cl.[7] .............................................. G06F 11/00
(52) U.S. Cl. ....................................................... 714/26
(58) Field of Search ........................................ 714/1–57

(56) References Cited

U.S. PATENT DOCUMENTS

| | | | | | |
|---|---|---|---|---|---|
| 4,853,946 | A | * | 8/1989 | Elliott et al. | 378/4 |
| 5,077,768 | A | * | 12/1991 | Shigyo et al. | 378/98 |
| 5,331,550 | A | * | 7/1994 | Stafford et al. | 382/128 |
| 5,463,768 | A |  | 10/1995 | Cuddihy et al. | |
| 5,805,160 | A | * | 9/1998 | Yoshida et al. | 345/339 |
| 6,025,717 | A | * | 2/2000 | Hertz et al. | 324/310 |
| 6,473,659 | B1 | * | 10/2002 | Shah et al. | 700/79 |

FOREIGN PATENT DOCUMENTS

EP 198 29 640 3/1999

\* cited by examiner

Primary Examiner—Nadeem Iqbal
Assistant Examiner—Timothy M. Bonura
(74) Attorney, Agent, or Firm—David C. Goldman; Noreen C. Johnson

(57) ABSTRACT

A system and method for diagnosing and validating a machine over a network using waveform data. Historical waveform data are obtained via the network from machines having known faults along with corresponding actions for repairing the machines and are used to develop fault classification rules. The fault classification rules are stored in a diagnostic knowledge database. The database of classification rules are used to diagnose new waveform data from a machine having an unknown fault, via the network.

35 Claims, 12 Drawing Sheets

| | | | | | |
|---|---|---|---|---|---|
| HEAD | FSE | XY | L33 | | R33 |
| | | YZ | P33 | | A33 |
| | | ZX | I33 | | S33 |
| | FGRE | XY | L33 | | R33 |
| | | YZ | P33 | | A33 |
| | | ZX | I33 | | S33 |
| BODY | FSE | XY | L78 | iso | R78 |
| | | YZ | P78 | iso | A78 |
| | | ZX | I1378 | iso | I1222 |
| | FGRE | XY | L78 | iso | R78 |
| | | YZ | P78 | iso | A78 |
| | | ZX | I1378 | iso | I1222 |

42

SYSTEM AND METHOD FOR DIAGNOSING AND VALIDATING A MACHINE OVER A NETWORK USING WAVEFORM DATA

CROSS-REFERENCE TO RELATED APPLICATIONS

This application is a continuation-in-part of U.S. patent application Ser. No. 09/050,143, entitled "System And Method For Diagnosing And Validating A Machine Using Waveform Data", filed Mar. 30, 199 now U.S. Pat. No. 6,105,149.

BACKGROUND OF THE INVENTION

The present invention relates generally to fault diagnosis and more particularly to using waveform data generated from a machine to provide diagnostics.

In either an industrial or commercial setting, a malfunctioning machine such as an imaging machine can impair a business severely. Thus, it is essential that a malfunctioning imaging machine be repaired quickly and accurately. Usually, during a malfunction of an imaging machine such as a computed tomography (CT) or a magnetic resonance imaging (MRI) machine, a field engineer is called in to diagnose and repair the machine. Typically, the field engineer will run a system performance test to analyze the image quality or the state of the imaging machine. The system performance test generates waveform data which provides a "signature" of the operation of the imaging machine. The waveform data comprises data sets of various readouts and slice combinations. After the system performance test has been run, the field engineer sends the data sets to a service engineer at a remote location for help in diagnosing the malfunction. The service engineer analyzes the data sets and uses their accumulated experience at solving imaging machine malfunctions to find any symptoms that may point to the fault. The field engineer then tries to correct the problem that may be causing the machine malfunction based on the diagnosis provided by the service engineer. If the data sets contain only a small amount of information, then this process will work fairly well. However, if the data sets contains a large amount of imprecise information, as is usually the case for large complex devices, then it is very difficult for the field engineer and the service engineer to quickly diagnose a fault. Therefore, there is a need for a system and method that can quickly diagnose a malfunctioning imaging machine from waveform data sets containing large amount of imprecise information.

SUMMARY OF THE INVENTION

One embodiment of the invention relates to a system and a method for diagnosing a machine from a remote facility over a network. In this embodiment, a diagnostic knowledge base contains a plurality of rules for diagnosing faults in a machine and a plurality of corrective actions for repairing the faults. A diagnostic fault detector categorizes the waveform data generated from the machine as normal and faulty data, wherein the machine is connected to the remote facility over the network. A diagnostic feature extractor extracts a plurality of features from the waveform data categorized as faulty data. A diagnostic fault isolator, coupled to the diagnostic feature extractor and the diagnostic knowledge base, isolates a candidate set of faults for the extracted features and identifies root causes most likely responsible for the candidate set of faults.

Another embodiment of the invention relates to a system and method for performing a validation of waveform data generated from a machine, from a remote facility over a network. The waveform data generated from the machine may be either run-time data or stand-by operation data. In this embodiment, a diagnostic knowledge base contains a plurality of rules for diagnosing faults in the machine. A diagnostic fault detector categorizes the waveform data as normal and faulty data. A diagnostic feature extractor extracts a plurality of features from the waveform data categorized as normal data.

DETAILED DESCRIPTION OF THE INVENTION

Figure 1:
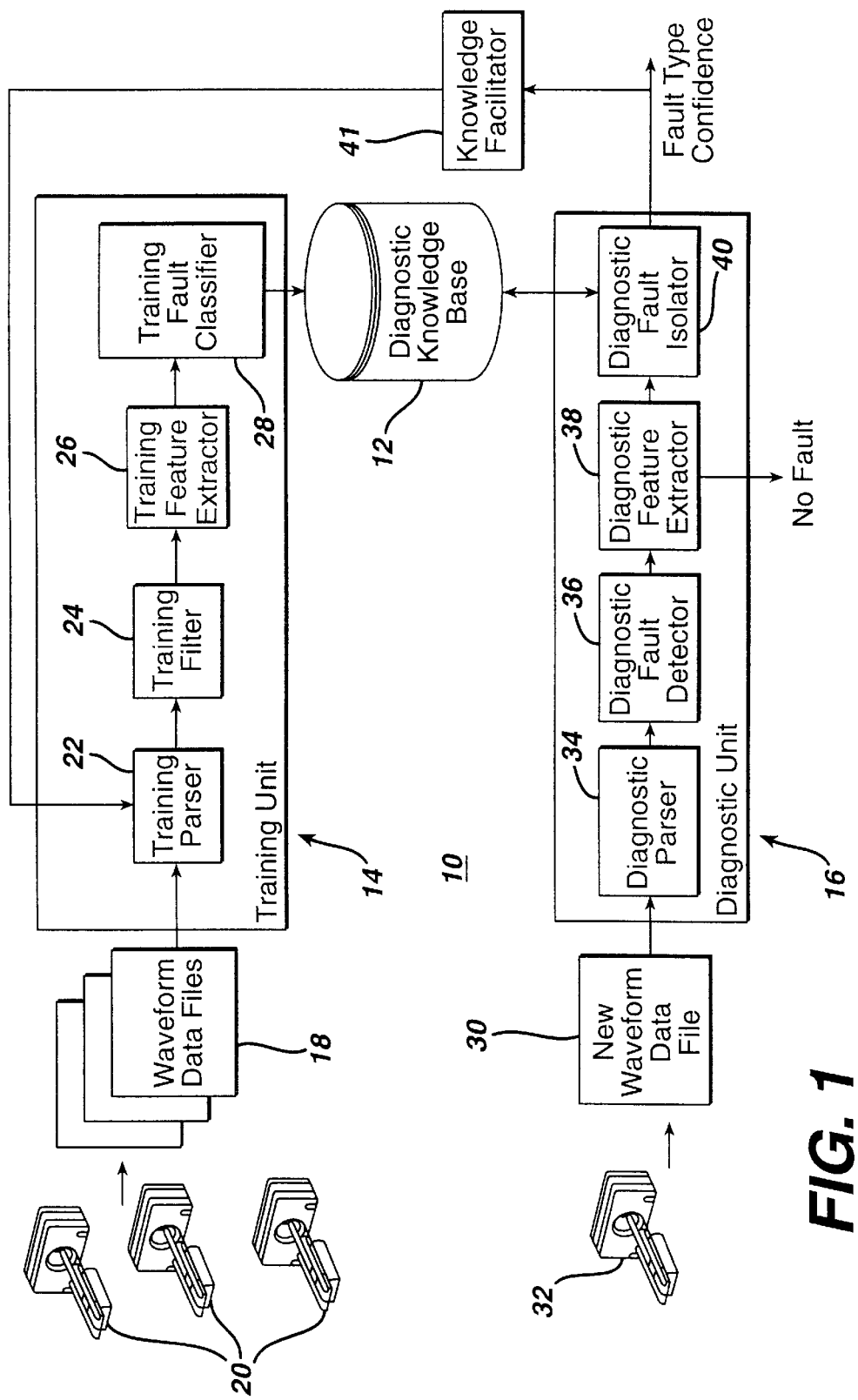
FIG. 1 shows a block diagram of a system for diagnosing an imaging machine according to a preferred embodiment.

The diagnosis system of this invention is described with reference to a medical imaging device such as a CT or a MRI machine. Although this invention is described with reference to a medical imaging device, the diagnosis system can be used in conjunction with any device (chemical, mechanical, electronic, microprocessor controlled) which generates waveform outputs. FIG. 1 shows a block diagram of a system 10 for diagnosing an imaging machine according to this invention. The diagnosis system 10 includes a diagnostic knowledge base 12 containing a plurality of rules for diagnosing faults in an imaging machine, a training unit 14, and a diagnostic unit 16. The training unit 14 obtains a plurality of sets of waveform data files 18 taken from a plurality of imaging machines 20. The training unit 14 includes a training parser 22 for removing extraneous data from each of the sets of waveform data, a training filter 24 for categorizing each of the sets of waveform data as normal and faulty data, and a training feature extractor 26 for extracting a plurality of features from each of the sets of waveform data categorized as faulty data, and a training fault classifier 28 for developing a plurality of steps that classify the extracted features into a fault characterization and providing the steps to the diagnostic knowledge base 12.

The diagnostic unit 16 obtains a new waveform data file 30 from an imaging machine 32. The diagnostic unit 16 includes a diagnostic parser 34 for removing extraneous data from the new waveform data, a diagnostic fault detector 36 for categorizing the new waveform data as normal and faulty data, a diagnostic feature extractor 38 for extracting a plurality of features from the new waveform data categorized as faulty data, and a diagnostic fault isolator 40 coupled to the diagnostic knowledge base 12, for isolating a candidate set of faults for the extracted features and identifying root causes most likely responsible for the candidate set. Both the training unit 14 and the diagnostic unit 16 are embedded in a computer such as a workstation. However other types of computers can be used such as a mainframe, a minicomputer, a microcomputer, or a supercomputer. The algorithms performed in both the training unit 14 and the diagnostic unit 16 are programmed in C++, JAVA, and MATLAB, but other languages may be used.

The candidate set of faults generated from the diagnostic unit 16 are presented to a knowledge facilitator 41, which in this invention is a service engineer. The service engineer examines the candidate set and determines if the fault for the MRI machine 32 has been correctly identified. If the fault has not been correctly identified, then the service engineer identifies the correct fault type and inputs the new waveform data and fault type information into the training unit 14 so that it can be used to identify future faults of a similar nature. In particular, the waveform data and fault type information are inputted to the training parser 22 for parsing, the training filter 24, the training feature extractor 26 and the training fault classifier 28.

The plurality of sets of waveform data files 18 generated from the plurality of MRI machines 20 are obtained from imaging phantoms. Each of the waveform data files 18 have known faults associated therewith. An illustrative but not exhaustive list of some of the known faults are inadequately compensated long time constant eddy currents, environmental magnetic field disturbances, magnitude and constant phase spikes caused by a body preamplifier, spikes caused by a defective IPG, high vibrations caused by rotating machinery on the floor above or below the magnet, failures caused by a defective Y-axis GRAM, and failures caused by a loose dynamic disable box RF connectors on the body coil.

Figure 2:
FIG. 2 shows an example of a data structure for a waveform data file according to the preferred embodiment.
Figure 3:
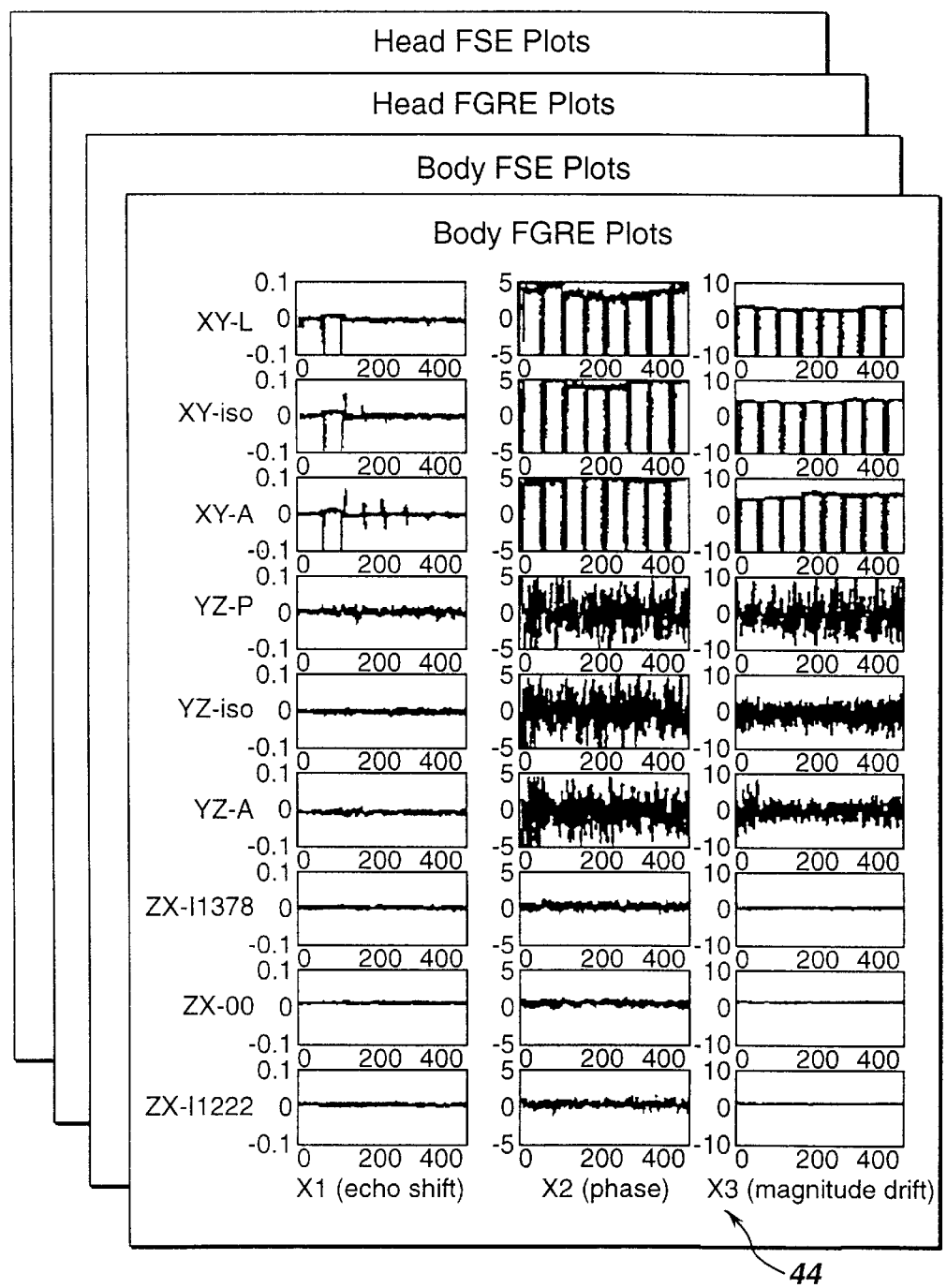
FIG. 3 shows an example of time series plots for the data sets represented by the data structure shown in FIG. 2.

The two areas of the phantoms that are scanned are the head and the body. A fast spin echo (FSE) test and a fast gradient test (FGRE) are run for both the head and the body. The FSE test has a high RF duty cycle which makes it more sensitive to RF related problems, while the FGRE test which stresses primarily the gradient drivers, is more sensitive to gradient related problems. These tests are then run at multiple locations to generate a complete data set. A complete data set comprises 90 data sets. The FGRE data contains 256 data points while the FSE data contains 512 data points. An example of a data structure 42 for a waveform data file 18 according to this invention is shown in FIG. 2. The data structure 42 is divided into two categories the head and the body. As mentioned above, for both the head and the body, a FSE and a FGRE test is run at various locations. For example, as shown in FIG. 2, a body FSE data set is taken at XY (X slice, Y readout) at L78 (left 78), iso (isocenter), and R78 (right 78). Other acronyms listed in FIG. 2 are P (posterior), A (anterior), I (inferior), and S (superior). The data acquired at the various locations for both the head FSE and FGRE and body FSE and FGRE are representative of three variables $x_1(t_j)$, $x_2(t_j)$, $x_3(t_j)$. The $x_1(t_j)$ variable is representative of the echo shift, the $x_2(t_j)$ variable is representative of the constant phase drift, and the $x_3(t_j)$ variable is representative of the magnitude drift, wherein $t_j$ indicates the $j^{th}$ time. The three variables $x_1(t_j)$, $x_2(t_j)$, $x_3(t_j)$ are sampled over time to create three time series plots 44 of n points. An example of a time series plots 44 for the head FSE, head FGRE, body FSE, and body FGRE are shown in FIG. 3.

Each waveform data file 18 is inputted into the training unit 14. The training parser 22 then extracts data from each file. A flow chart setting forth the steps performed by the training parser 22 is set forth in FIG. 4. The training parser begins by obtaining one of the waveform data files at 46 for each historical case. The header information (i.e., system hardware, software version, site of the MRI, type of MRI, manufacturing date, date stamp, etc.) is retrieved and saved into an information file at 48. For each block of data in the file, the waveform data is extracted at 50 and saved into a parsed file at 52. If all of the waveform data files have been parsed then this process ends.

Figure 5:
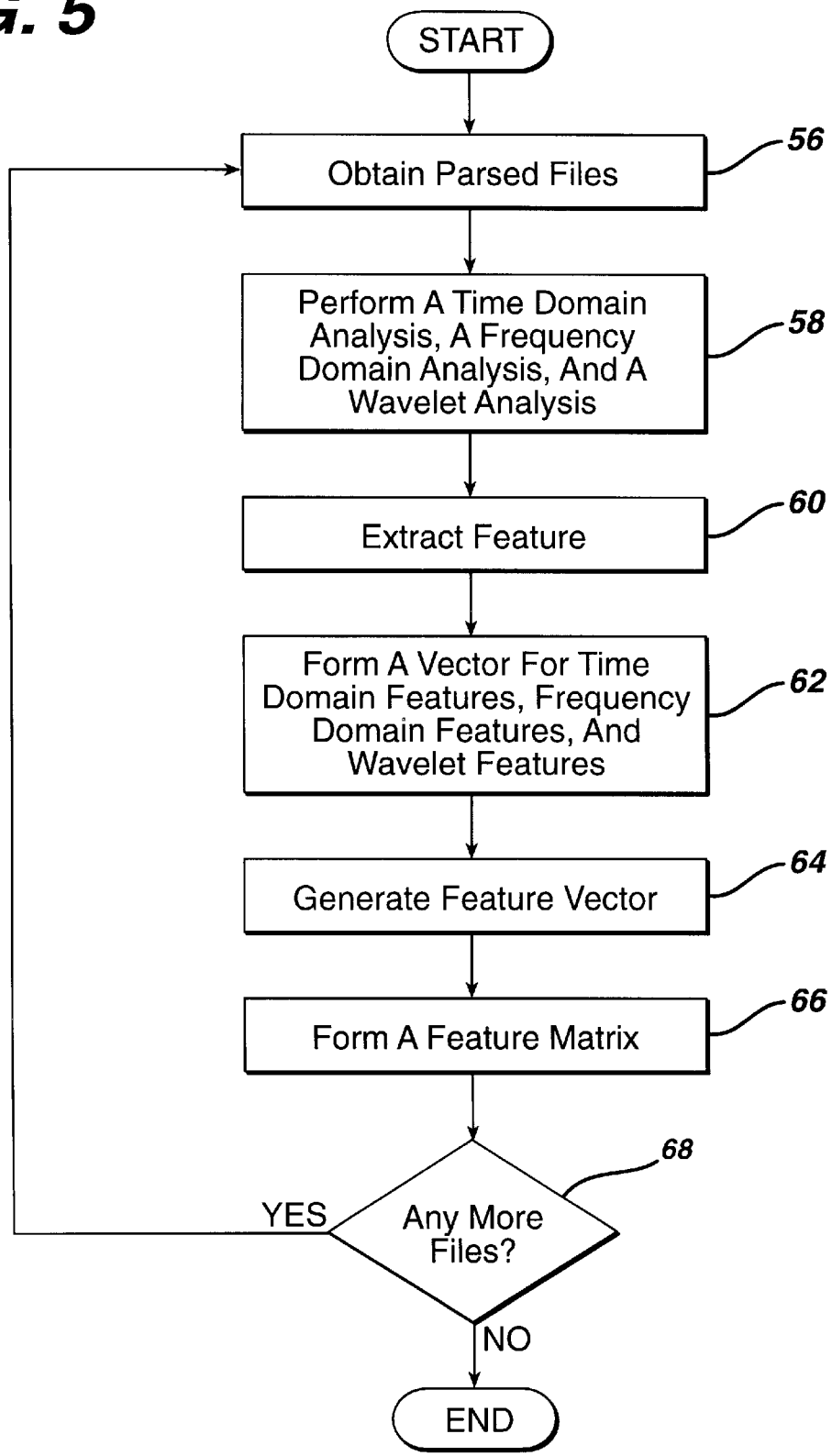
FIG. 5 shows a flow chart setting forth the steps performed by the training filter and the training feature extractor shown in FIG. 1.

After each waveform data file 18 has been parsed for data and information, the files are then applied to the training filter 24 for preprocessing and the training feature extractor 26 for further processing. FIG. 5 shows a flow chart setting forth the steps performed by the training filter 24 and the training feature extractor 26. In this invention the training filter is a gross filter and a fine filter. At 56, the training filter obtains a waveform data file from the training parser. For each file, the training filter performs a time domain analysis, a frequency domain analysis, and a wavelet analysis at 58. For the time domain analysis, time series data is used to compute peak-to-peak values in a graph, the area under a curve (integral) in the graph, and the slope of a curve (derivative). The frequency domain analysis uses the Fast Fourier Transform (FFT) to decompose a time-series plot of data into different frequency components for analyzing relative magnitudes. The wavelet analysis is achieved by using a discrete wavelet transform (DWT) which is the counterpart of the FFT. Like the FFT, the DWT requires that the number of samples to be a power of two. The DWT analyzes the signal at different time scales or resolutions. With a large window, "gross" features can be noticed, while with a small window, "small" features like spikes can be noticed. In the DWT, the signal is approximated by a finite sum of coefficients $W_i$ that multiply scaled versions of the mother wavelet (the original basis function).

The time domain analysis, frequency domain analysis, and wavelet analysis are used to extract features at 60. If desired, a data visualizer routine may be applied to the data that remains after performing the time domain analysis, frequency domain analysis, and wavelet analysis in order to allow a service engineer to visualize all of the time series plots for the head FSE, head FGRE, body FSE, and body FGRE. The features that are extracted from the time domain analysis are:

the minimum of the time series which is defined as:

$$v_{1,i} = \min_{j=1}^{n} x_i(t_j); \tag{1}$$

the maximum value of the time series which is defined as:

$$v_{2,i} = \max_{j=1}^{n} x_i(t_j); \quad (2)$$

the peak-to-peak distance of the time series which is defined as:

$$v_{3,i} = v_{2,i} - v_{1,i}; \quad (3)$$

the time series average which is defined as:

$$v_{4,i} = \frac{\sum_{j=1}^{n} x_i(t_j)}{n}; \quad (4)$$

the standard deviation of the time series which is defined as:

$$v_{5,i} = \sqrt{\frac{\sum_{j=1}^{n} (x_i(t_j) - v_{4,i})^2}{n-1}}; \quad (5)$$

the minimum absolute value of the time series during the first 64 samples which is defined as:

$$v_{6,i} = \min_{j=1}^{64} |x_i(t_j)|; \quad (6)$$

the time of minimum value for the first 64 samples which is defined as:

$$v_{7,i} = j_{min}, \text{ wherein } x_i(t_{jmin}) = v_{6,i}; \quad (7)$$

the sign of the minimum value for the first 64 samples which is defined as:

$$v_{8,i} = \text{sign}\{x_i(t_{jmin})\}, \text{ wherein } x_i(t_{jmin}) = v_{6,i}; \quad (8)$$

the maximum absolute value of the time series during the first 64 sample which is defined as:

$$v_{9,i} = \max_{j=1}^{64} |x_i(t_j)|; \quad (9)$$

the time of the maximum value for the first 64 samples which is defined as:

$$v_{10,i} = j_{max}, \text{ wherein } x_i(t_{jmax}) = v_{9,i}; \quad (10)$$

the sign of the maximum value for the first 64 samples which is defined as:

$$v_{11,i} = \text{sign}\{x_i(t_j \max)\} \text{ where } x_i(t_{jmax}) = v_{9,i}; \text{ and} \quad (11)$$

the slope of the line segment approximating the time series derivative during the first 64 samples which is defined as:

$$v_{12,i} = \frac{(x_i(t_{64}) - x_i(t_1))}{63} \quad (12)$$

The features that are extracted from the frequency domain analysis are:
the maximum amplitude of the power spectrum which is defined as:

$$v_{13,i} = \max_{j=1}^{n} A_j, \quad (13)$$

wherein $A_j$ is the $j^{th}$ amplitude of the FFT of $x_i(t_j)$;

the frequency at which the maximum amplitude occurs which is defined as:

$$v_{14,i} = \max_{j=1}^{n} F_j, \quad (14)$$

wherein $F_j$ is the $j^{th}$ frequency component of the FFT of $x_i(t_j)$; and the total power which is defined as:

$$v_{15,i} = \sum_{j=1}^{n} C_j^2, \quad (15)$$

wherein $C_j$ is the $j^{th}$ coefficient of the FFT of $x_i(t_j)$.

The features that are extracted from the wavelet analysis are determined after all of the coefficients of the wavelet transform $W_i$ have been computed. The first wavelet feature is the maximum absolute value among all spikes. This feature is applied to the points in the scatter plot of the last two wavelet coefficients ($W_{n,i}$, $W_{n-1,i}$). Since these coefficients are good indicators of spikes, the energy contained in a spike is not considered to be noticeable on the full-length time window used by the mother wavelet or by an FFT. However, the energy contained in the spike can be considerable and easy to detect once it is compared with the rest of the signal in a very reduced time window. In order to determine the maximum absolute value among all spikes, the centroid coordinates of the clustered data must first be computed. The centroid coordinates of the clustered data is defined as:

$$(C_k, C_{k-1}) = \left( \frac{\sum_{j=1}^{n} W_k^j}{n}, \frac{\sum_{j=1}^{n} W_{k-1}^j}{n} \right)$$

Next, all the outliers (i.e., points that are considerably far from the centroid of clustered data) in the scatter plot are identified. The outliers are identified as:

$$d_{1,i} = \sqrt{(W_{k,i} - C_k)^2 + (W_{k-1,i} - C_{k-1})^2}$$

Next, three standard deviation is used as the threshold for the outliers. Alternatively, filtering may be used to remove some noise for the weak signal around zero. Finally, the outlier that is the furthest away from the centroid, i.e., is considered to be the strongest spike which is defined as:

$$v_{16,i} = \max_j d_{1,i}^j \quad (16)$$

The next wavelet feature that is determined is the sign of the strongest spike which is defined as:

$$v_{17,i} = \text{sign}\{W_{k,jmax}\}, \quad (17)$$

$$\sqrt{(W_{k,j_{max}} - C_k)^2 + (W_{k-1,j_{max}} - C_{k-1})^2} = v_{16,i}$$

Another wavelet feature that is determined is the time at which the strongest spike occurs which is defined as:

$$v_{18,i} = j_{max} \quad (18)$$

$$\sqrt{(W_{k,j_{max}} - C_k)^2 + (W_{k-1,j_{max}} - C_{k-1})^2} = v_{16,i}$$

Still another wavelet feature that is determined is the number of spikes which is defined as:

$$v_{19,i} = \sum_{j=1}^{k} d_{1,j}, \quad (19)$$

wherein $d_{1,j}$ is greater than 3 standard deviation.

Referring back to FIG. 5, after the features have been extracted, then a vector is formed for a file at 62 for the time domain features, frequency domain features, and the wavelet features. Next, the vectors are combined at 64 to yield a feature vector. The feature vector represents in a feature space, the time-series values of each of the variables $x_1(t_j)$, $x_2(t_j)$, $x_3(t_j)$. After all of the features have been extracted, then the feature vectors are placed into a feature matrix at 66. In this invention, the feature matrix would be a 90×19 matrix. If it is determined at 68 that there are more files, then steps 56–66 are repeated until features have been extracted for all files.

Figure 6:
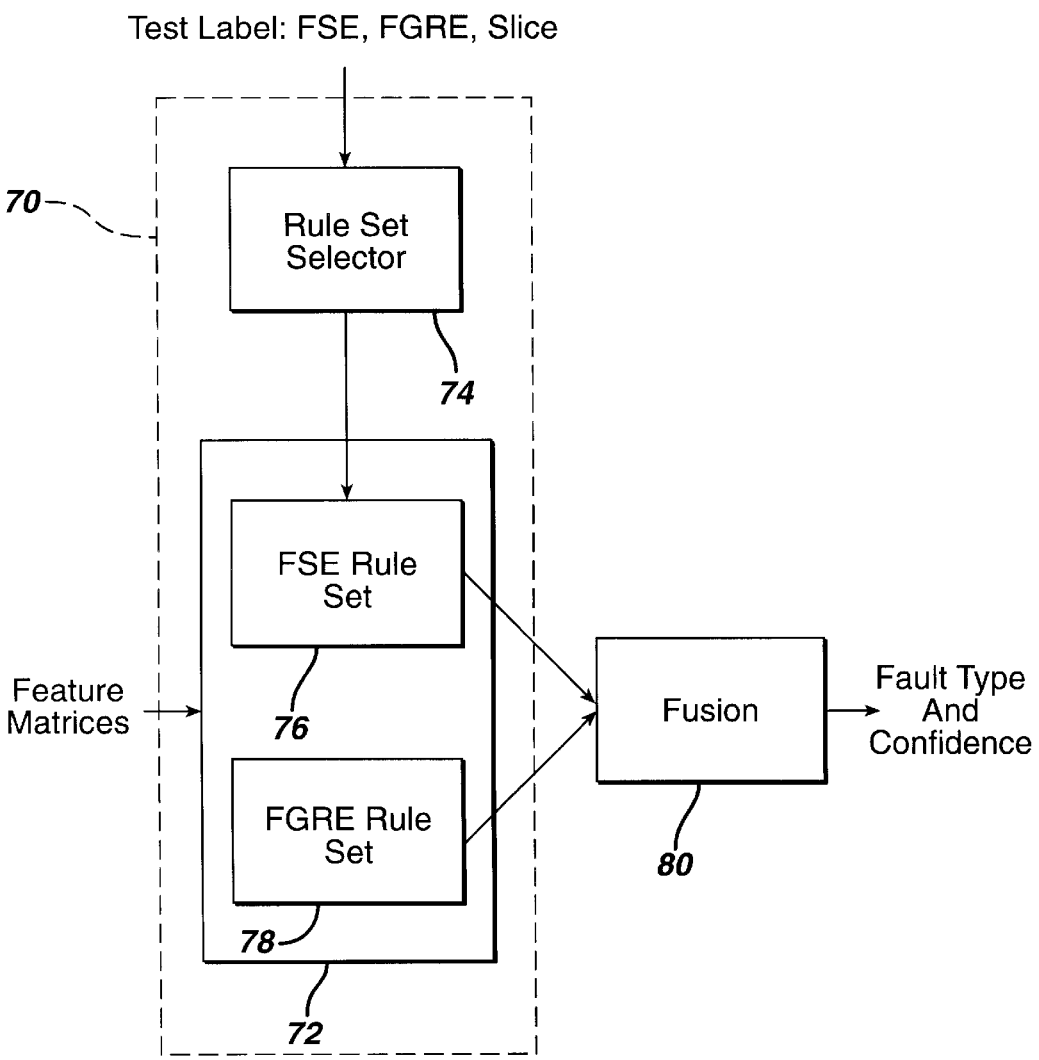
FIG. 6 shows a block diagram of a more detailed view of the training fault classifier shown in FIG. 1.

After the features have been extracted from all of the waveform data files, the features are then applied to the training fault classifier 28 where the plurality of rules are developed. The rules are used to classify the feature matrices into a particular fault characterization. FIG. 6 shows a block diagram of the training fault classifier 28 in more detail. The training fault classifier comprises an expert system 70 having a rule base 72 and a rule selector 74 for selecting the most applicable steps from the rule base. The rule base 72 comprises a FSE rule set 76 and a FGRE rule set 78. Both the FSE and FGRE rule set are based on an IF-THEN rules defined for the following example faults:

$f_1$: Inadequately compensated long time constant eddy currents;

$f_2$: Environmental magnetic field disturbances;

$f_3$: Magnitude and constant phase spikes;

$f_4$: Spikes caused by a defective IPG;

$f_5$: High vibration caused by rotating machinery on the floor;

$f_6$: Failures caused by a defective Y-axis GRAM; and $f_7$: Failures caused by a loose dynamic disable box RF connectors.

This invention is not limited to these faults and other possible faults may be a RF receive fault, a RF transmit fault, a RF receive and transmit fault, a shim fault, a S-V magnet signature fault, a steady state disturbance (i.e., vibration), a gradient axis fault, a magnet disturbance, a steady state disturbance (i.e., cold heads and magnetic anomaly, a transient vibration, a SNR having a low signal, and a SNR having high noise.

In this invention, the faults $f_1$–$f_7$, are identified by using the following rules:

$R_{1A} \rightarrow f_1$ applicable for slice Y, readout Z;

$R_{1B} \rightarrow f_1$ applicable for slice Z, readout X;

$R_{2A} \rightarrow f_2$ applicable for slice X, readout Y;

$R_{2B} \rightarrow f_2$ applicable for slice Y, readout Z;

$R_{3A} \rightarrow f_3$ applicable for FSE;

$R_{3B} \rightarrow f_3$ applicable for FGRE;

$R_{4A} \rightarrow f_4$ applicable for FSE;

$R_{4B} \rightarrow f_4$ applicable for FGRE;

$R_5 \rightarrow f_5$ applicable for FSE;

$R_{6A} \rightarrow f_6$ applicable for FSE;

$R_{6B} \rightarrow f_6$ applicable for FGRE;

$R_{7A} \rightarrow f_7$ applicable for FSE; and $R_{7B} \rightarrow f_7$ applicable for FGRE The linguistic rules for $R_{1A}$–$R_{7B}$ are as follows:

$R_{1A}$: regardless of location, $x_1$ shows a discharge in the first 64 samples, while $x_2$ and $x_3$ are normal;

$R_{1B}$: regardless of location (except for ISO), $x_2$ shows a discharge in the first 64 samples, while $x_1$ and $x_3$ are normal;

$R_{2A}$: regardless of location, $x_2$ shows large excursions, while $x_1$ and $x_3$ are normal;

$R_{2B}$: regardless of location, $x_2$ shows very large excursions, while $x_1$ and $x_3$ are almost normal;

$R_{3A}$: $x_2$ and $x_3$ show only one spike, of opposite sign, at about the same time, while $x_1$ is normal;

$R_{3B}$: $x_2$ and $x_3$ show only one spike, of opposite sign, at about the same time, while $x_1$ is normal;

$R_{4A}$: $x_1$, $x_2$ and $x_1$ show two spikes, one spike that propagates a second time, wherein the spikes occur at about the same time across all three variables;

$R_{4B}$: $x_1$, $x_2$ and $x_3$ show two spikes, one spike that propagates a second time, wherein the spikes occur at about the same time across all three variables;

$R_5$: $x_2$ shows a large number of spikes in both directions, while $x_1$ and $x_3$ are normal;

$R_{6A}$: except for the ISO location, $x_2$ shows repeated spikes, all in the same direction, furthermore the spikes in $x_2$ are of opposite direction on opposite sides of the isocenter; meanwhile, $x_1$ is normal and $x_3$ is assumed to be equally normal, although it is not available in the data sets;

$R_{6B}$: except for the ISO location, $x_1$ shows repeated spikes, all in the same direction, while $x_2$ and $x_3$ is normal;

$R_{7A}$: except for the ISO location, $x_2$ and $x_3$ show a large number of spikes, in the opposite direction, while $x_1$ shows numerous small spikes; and $R_{7B}$: large spikes in $x_2$.

Each of the above rules have a conjunction of predicates defining the set of conditions that must be satisfied to determine if the rule is true given the data. The rules are satisfied when all of its terms have been fulfilled, i.e., when all underlying constraints have been satisfied by the waveform data. In this invention, some of the terms in the rules $R_{1A}$–$R_{7B}$ have the following meaning:

discharge: is the derivative in the first 64 samples [$v_{9,i}$] coupled with the minimum and maximum values in the same first 64 samples [$v_{6,i}$, $v_{7,i}$];

nornal: means that the total power [$v_{12,i}$] is small and there is no spikes of large magnitude;

almost nonnal: means that there is noise on top of a normal signal;

large excursion: means that the range is greater than five or six standard deviations (2.5–3.0 sigmas on each side of the mean);

very large excursion: means that the range is greater than seven or eight standard deviations (3.5–4.0 sigmas on each side of the mean)

only one spike: is obtained from the presence of a spike via $v_{16,i}$ and the number of spikes $v_{19,i}=1$;

spikes of opposite sign: are obtained by applying $v_{17,i}$ to the feature vector of $x_i$ and $x_j$ and verifying that the two signs are opposite;

about the same time: is when two events occur within a short period of time (generally in 3 to 5 time steps); this is determined by applying $v_{18,i}$ to the two variables $x_i$ and $x_j$ and verifying that the time of the spike is within this small time window;

two spikes: is obtained by detecting the presence of a spike via $P_{1,i}$ and when the number of spikes $v_{19,i}=2$;

repeated spikes: are two successive spikes with similar magnitude within a finite period of time;

numerous small spikes: are a number of points with small magnitude are more than 3 sigma away from the centroid of the clustered data in the scatter plot of the last two wavelet coefficients; and large number of spikes: are a number of points with relative large magnitude which are far away from the centroid of the clustered data in the scatter plot of the last two wavelet coefficients.

The rules $R_{1A}$–$R_{7B}$ are then reformulated into IF-THEN rules and stored in the FSE rule set 76 and the FGRE rule set 78. For example, $R_{3A}$ for the FSE mode would be formulated as IF $x_2$ and $x_3$ show only one spike, of opposite sign, at about the same time, while $x_1$ is normal, THEN fault is $f_3$. The other rules would be formulated in a similar manner.

Referring back to FIG. 6, after the rule sets have been developed, a fusion module 80 uses the rules along with information such as the extracted feature matrices, the FSE, the FGRE, and the slice data to determine the fault type. In addition, the fusion module 80 considers other factors such as the amount of data available, the number of locations that the data was taken at, multiple slice locations provides a confidence value that is indicative of the confidence in declaring the fault type. Essentially, the completeness of the data is a major factor in determining the confidence in the fault classification and characterization. For instance, if there is only body FSE data and body FGRE data, then the confidence value would be 0.5. After the fault types and confidence values are assigned, then these values can be used by a service engineer to identify the root causes most likely responsible for the faults by a fault type and confidence value routine. In addition, the service engineer can use this information to determine the recommended fixes for correcting the faults.

Figure 7:
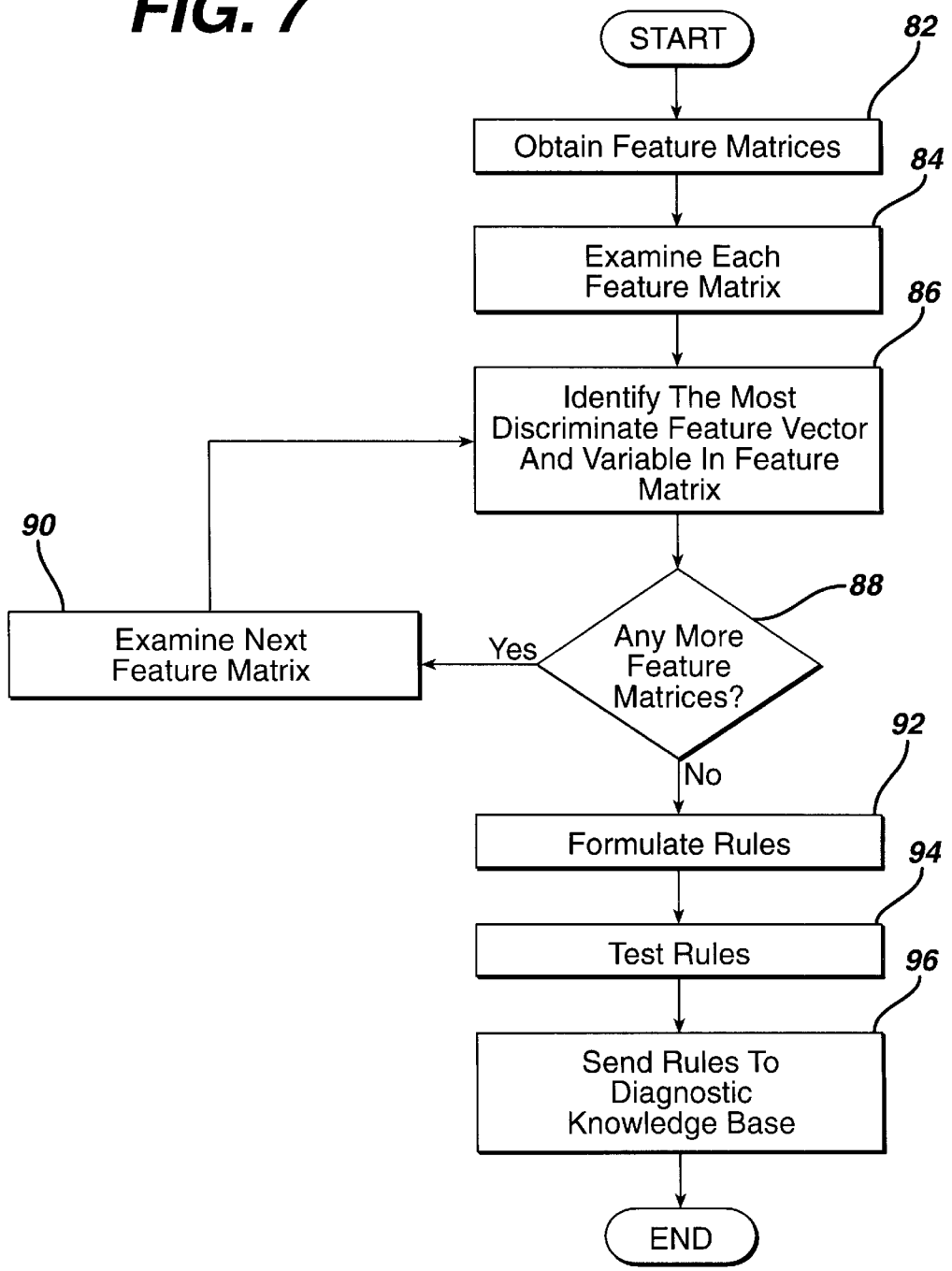
FIG. 7 shows a flow chart setting forth the processing steps performed by the training fault classifier.

FIG. 7 shows a flow chart setting forth the processing steps performed by the training fault classifier 28. The processing steps begin at 82 where all of the feature matrices are obtained from the training feature extractor. Each feature matrix is then examined at 84. The most discriminate features and variables in the matrix are then identified at 86. In particular, the feature vectors are examined to determine if a particular variable exceeds a predetermined threshold. If it is determined that there are more feature matrices at 88, then the next feature matrix is retrieved at 90 and examined at 86 to determine the most discriminate feature vector and variable. This process continues until all of the feature matrices have been examined. The discriminate feature vectors and variables are then used to formulate the FSE rule set and the FGRE rule set at 92. In order to ensure that the rule sets will work on new set of waveform data, the rules are tested at 94. After the rule sets have been tested, then the rules are sent to the diagnostic knowledge base at 96.

After the rule sets have been sent to the diagnostic knowledge base 12, then the diagnostic unit 16 is ready to be used to diagnose new waveform data from MRI machines having unknown faults. Referring back to FIG. 1, the diagnostic unit 16 receives the new waveform data file 30 generated from the MRI machine 32 experiencing an unknown fault. The new waveform data file 30 is inputted to the diagnostic unit 16 at the diagnostic parser 34 by either a service engineer or by a remote dial-in connection by a field engineer.

Figure 4:
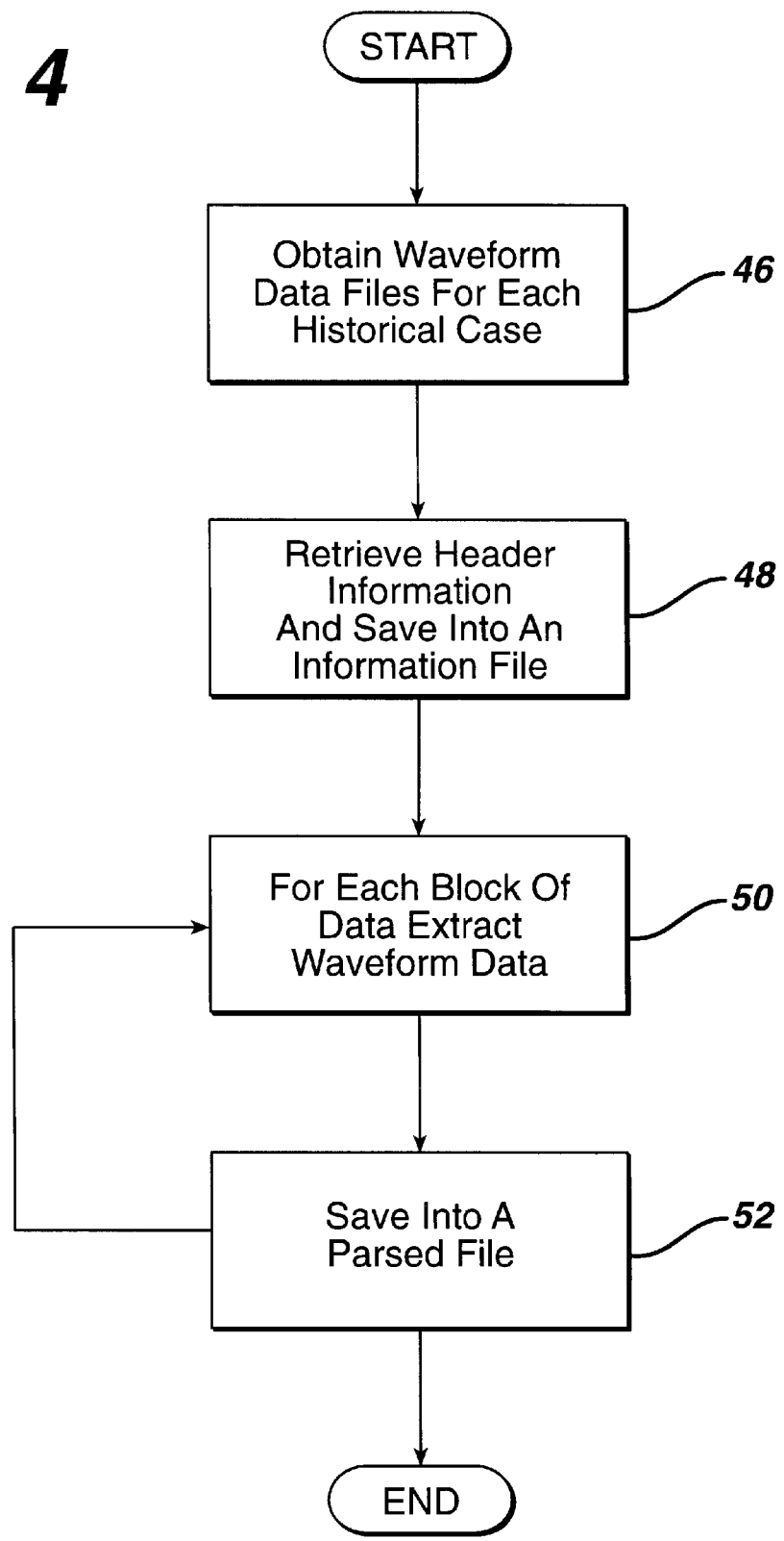
FIG. 4 shows a flow chart setting forth the steps performed by the training parser shown in FIG. 1.

The steps performed by the diagnostic parser 34 are substantially the same as the steps for the training parser 22 which are set forth in FIG. 4. Essentially, the diagnostic parser 34 extracts blocks of data from the new waveform data file 30 and saves it in a file for each slice-readout and location data set. In addition, an information file is created for the header which contains information about the system hardware, software version, magnet type, site information, date stamp, and other relevant information. After the new waveform data file 30 has been parsed, the file is then applied to the diagnostic fault detector 36 for preprocessing. Like, the training filter 24, the diagnostic fault detector 36 is a gross filter and fine filter that categorizes the new waveform data as normal and faulty data. In particular, a time domain analysis, a frequency domain analysis, and a wavelet analysis are performed on each block of data. In addition to filtering, a data visualizer routine may be applied to the parsed data file in order to allow a field/service engineer to visualize all of the time series plots for the head FSE, head FGRE, body FSE, and body FGRE.

After the time domain analysis, a frequency domain analysis, and a wavelet analysis have been performed, the diagnostic feature extractor 38 extracts a plurality of feature vectors for each block and puts the feature vectors into a feature matrix. In instances where the diagnostic fault detector categorizes the waveform data as normal, then the diagnostic unit 16 outputs that the operation of the machine has no fault. This aspect of the invention is well suited for performing a validation of the waveform data that is generated in either a run-time mode or stand-by operation mode. However, for faulty data, the extracted feature matrix is then applied to the diagnostic fault isolator 40 which operates in conjunction with the diagnostic knowledge base 12 to isolate a candidate set of faults. In this invention, the diagnostic fault isolator 40 is a rule-based reasoning expert system. Like the training fault classifier, the diagnostic fault isolator 40 comprises an expert system having a rule base (FSE rule set and a FGRE rule set) and a rule selector for selecting the most applicable rules from the rule base. Alternatively, other types of artificial reasoning techniques may be used such as case based reasoning, inference classification (i.e., linear classifiers, neural networks, rule based classifiers, and distance classifiers), and fuzzy reasoning.

Figure 8:
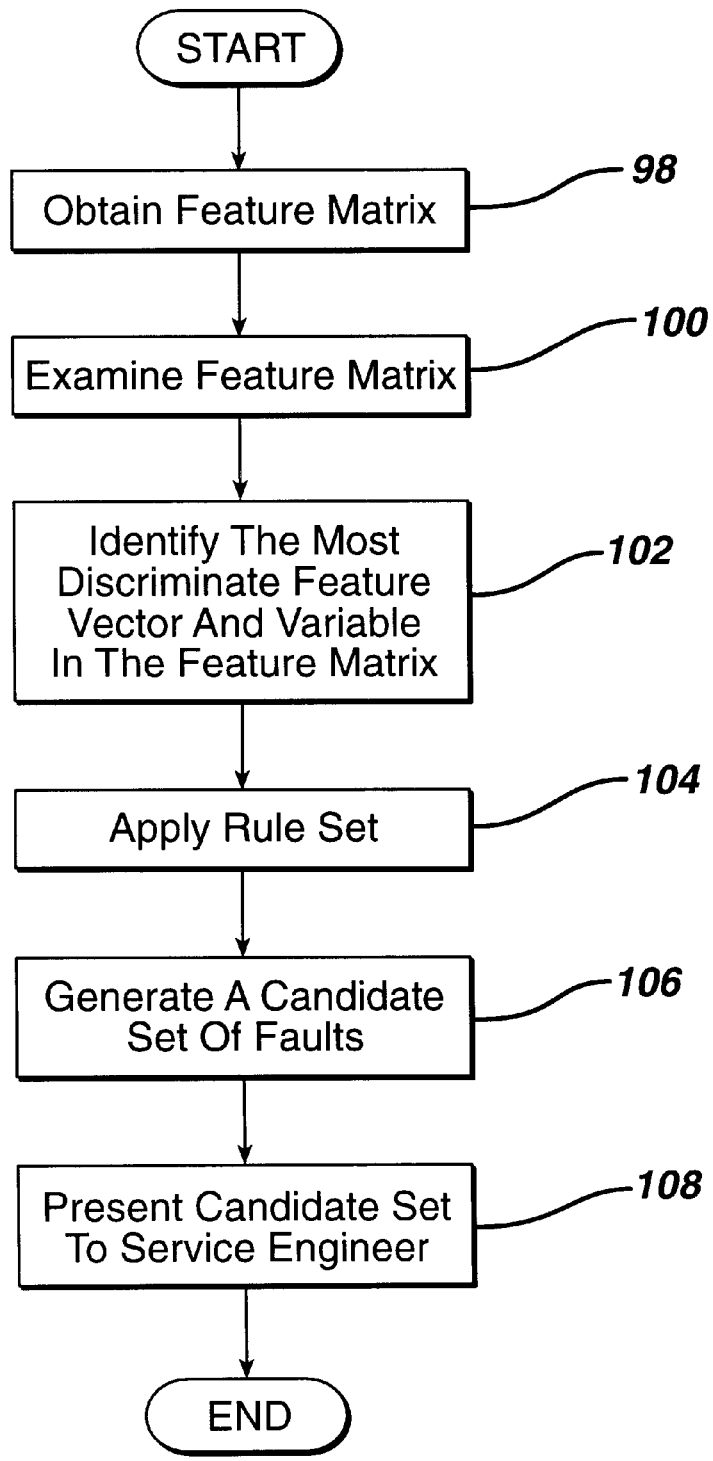
FIG. 8 shows a flow chart setting forth the fault isolation processing steps performed by the diagnostic unit shown in FIG. 1.

FIG. 8 shows a flow chart setting forth the fault isolation processing steps performed by the diagnostic fault isolator 40. The processing steps begin at 98 where the feature matrix is obtained from the diagnostic feature extractor 38. The feature matrix is then examined at 100. The most discriminate features and variables in the matrix are then identified at 102. In particular, the feature vector is examined to determine if a particular variable exceeds a predetermined threshold. Next, the rule set in the diagnostic knowledge base is applied to the feature matrix at 104. The rules are applied in accordance with the features that were identified as most discriminate and are used to generate a candidate set of faults at 106 that may be responsible for the fault associated with the MRI machine 32.

The candidate set of faults are then presented to a service engineer along with a respective confidence value indicating a belief that the fault is most likely responsible for the fault. The service engineer then examines the candidate set and determines if the fault for the MRI machine 32 has been correctly identified. If the fault has not been correctly identified, then the service engineer identifies the correct fault type and inputs the new waveform data into the training unit 14 for identifying future faults. In particular, the waveform data and fault type information are inputted to the training parser 22 for parsing, the training filter 24, the training feature extractor 26 and the training fault classifier 28.

Figure 9:
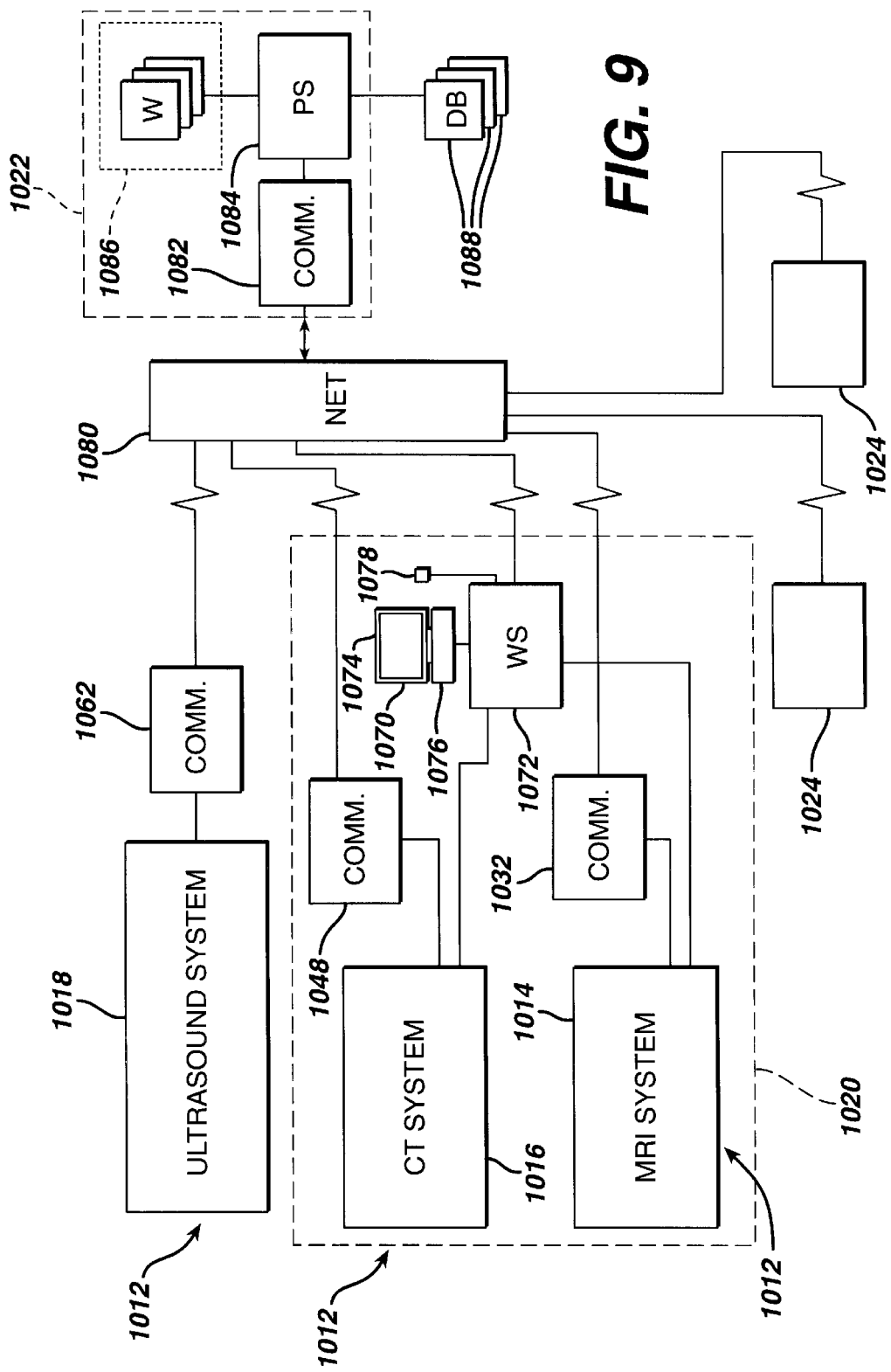
FIG. 9 is a diagrammatic representation of a series of medical diagnostic systems coupled to a service facility via a network connection for providing remote services and data interchange between the diagnostic systems and the service facility.

Referring now to FIG. 9, a service system 1010 is illustrated for providing remote service to a plurality of medical diagnostic systems 1012, including systems such as the diagnosis system 10 illustrated in FIG. 1. In the embodiment illustrated in FIG. 9, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

In the exemplary embodiment of FIG. 9, several different system modalities are provided with remote service by the service facility. Remote services include but are not limited to services, such as, remote monitoring, remote system control, immediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors. In general, however, the present technique is particularly well suited to providing remote service to a wide variety of medical diagnostic system modalities, including MRI systems, CT systems, ultrasound systems, positron emission tomography (PET) systems, nuclear medicine systems, and so forth. Moreover, the various modality systems serviced in accordance with the present techniques may be of different type, manufacture, and model.

Depending upon the modality of the systems, various subcomponents or subsystems will be included. In the case of MRI system 1014, such systems will generally include a scanner, a control and signal detection circuit, a system controller, and an operator station. MRI system 1014 includes a uniform platform for interactively exchanging service requests, messages and data with service facility 1022 as described more fully below. MRI system 1014 is linked to a communications module 1032, which may be included in a single or separate physical package from MRI system 1014. In a typical system, additional components may be included in system 1014, such as a printer or photographic system for producing reconstructed images based upon data collected from the scanner.

Similarly, CT system 1016 will typically include a scanner, a signal acquisition unit, and a system controller. The scanner detects portions of x-ray radiation directed through a subject of interest. The controller includes circuitry for commanding operation of the scanner and for processing and reconstructing image data based upon the acquired signals. CT system 1016 is linked to a communications module 1048 for transmitting and receiving data for remote services. Moreover, like MRI system 1014, CT system 1016 will generally include a printer or similar device for outputting reconstructed images based upon data collected by the scanner.

In the case of ultrasound system 1018, such systems will generally include a scanner and data processing unit and a system controller. Ultrasound system 1018 is coupled to a communications module 1062 for transmitting service requests, messages and data between ultrasound system 1018 and service facility 1022.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics.

Where more than one medical diagnostic system is provided in a single facility or location, as indicated in the case of MRI and CT systems 1014 and 1016 in FIG. 9, these may be coupled to a management station 1070, such as in a radiology department of a hospital or clinic. The management station may be linked directly to controllers for the various diagnostic systems. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless can be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed. Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain types of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally by reference numeral 1084 in FIG. 9. The processing system manages the receipt, handling and transmission of service data to and from the service facility. In general, processing system 1084 may include one or a plurality of computers, as well as dedicated hardware or software servers for processing the various service requests and for receiving and transmitting the service data as described more fully below.

Service facility 1022 also includes a bank of operator workstations 1086, which may be staffed by personnel who address the service requests and provide off and on-line service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment.

Figure 10:
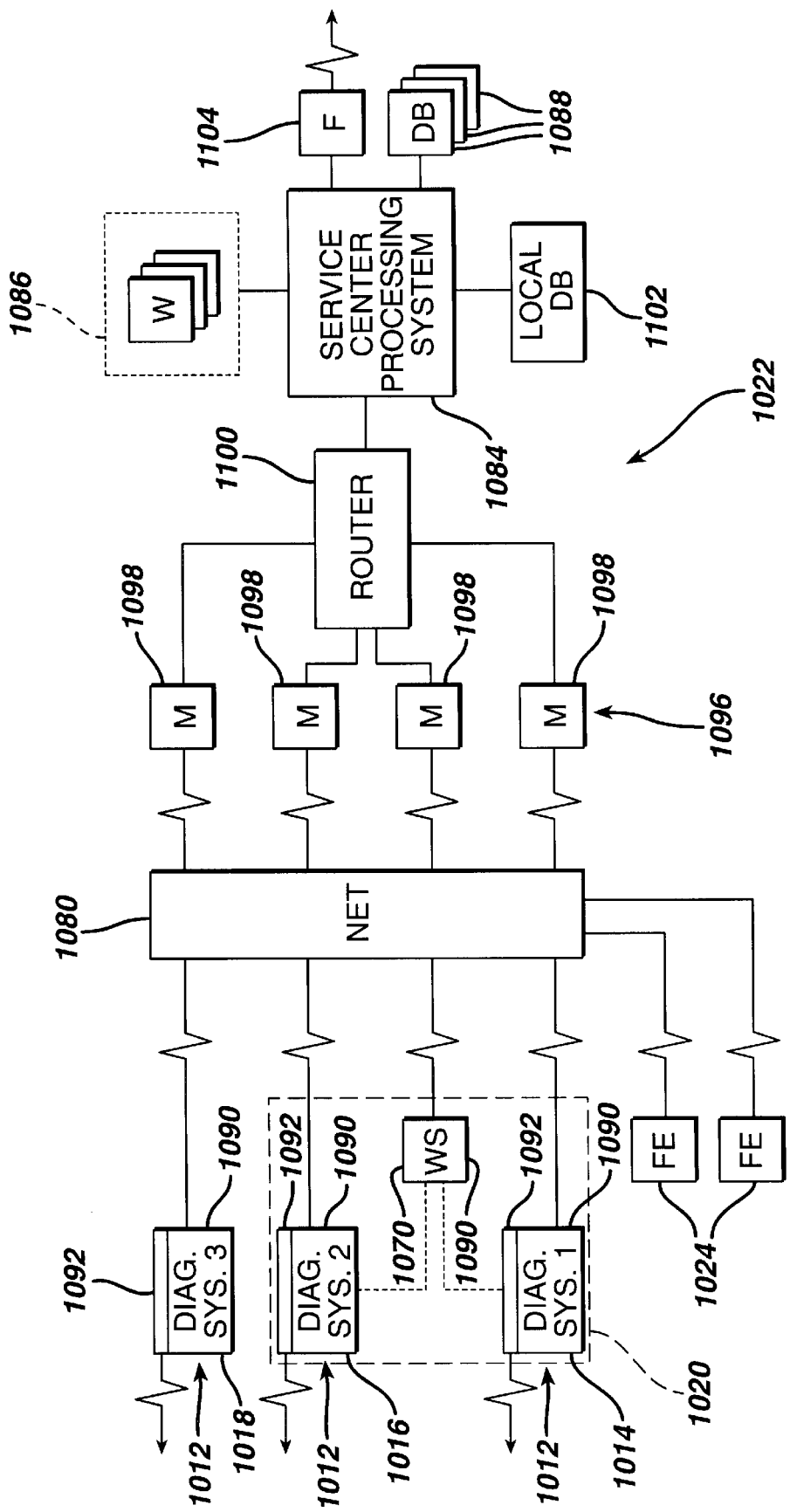
FIG. 10 is a block diagram of the systems shown in FIG. 9 illustrating certain functional components of the diagnostic systems and the service facility.

FIG. 10 is a block diagram illustrating the system components of FIG. 9 in a functional view. As shown in FIG. 10, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 11, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access images, log into and access similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the service facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 11000 which manages data traffic between the modems and the service center processing system 1084.

In the diagram of FIG. 10, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 11:
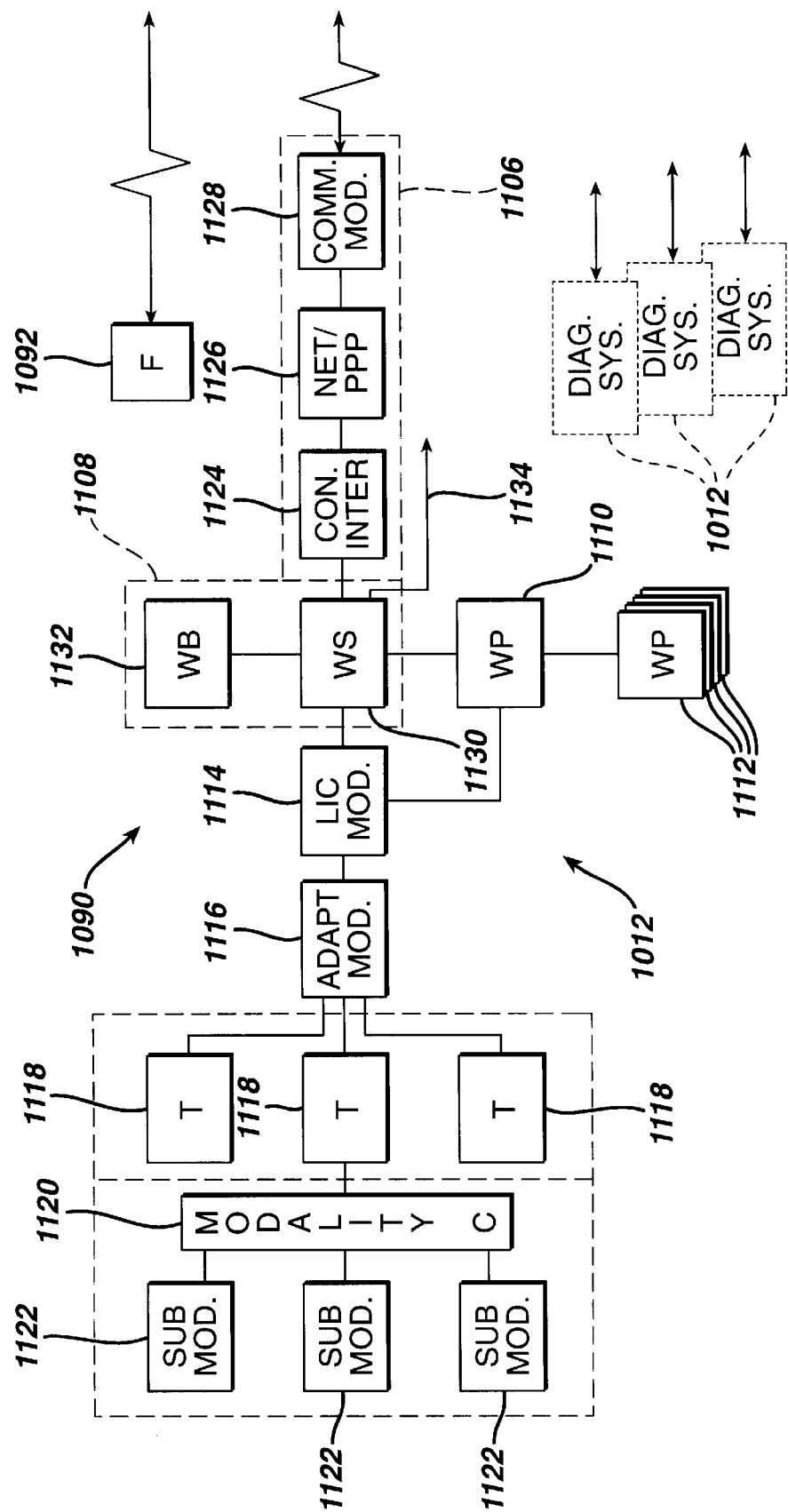
FIG. 11 is a block diagram of certain functional components within a diagnostic system of the type shown in FIGS. 9 and 10 for facilitating interactive remote servicing of the diagnostic system.

FIG. 11 illustrates diagrammatically the various functional components comprising the uniform service platform 1090 within each diagnostic system 1012. As shown in FIG. 11, the uniform platform includes a device connectivity module 1106, as well as a network connectivity module 1108. Network connectivity module 1108 accesses a main web page 1110 which, as mentioned above, is preferably a markup language page, such as an HTML page displayed for the system user on a monitor at the diagnostic system. Main web page 1110 is preferably accessible from a normal operating page in which the user will configure examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, per, Java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manage by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a preconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Poirit Protocol (PPP) module 1126 is also provided for transmitting Internet Protocol (IP) packets over remote communication connections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports Java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 9 and 10).

In a present embodiment, the components comprising network connectivity module may be configured via an application stored as part of the uniform platform.

In particular, a Java application licensed to a service engineer enables the engineer to configure the device connectivity at the diagnostic system to permit it to connect with the service facility.

Figure 12:
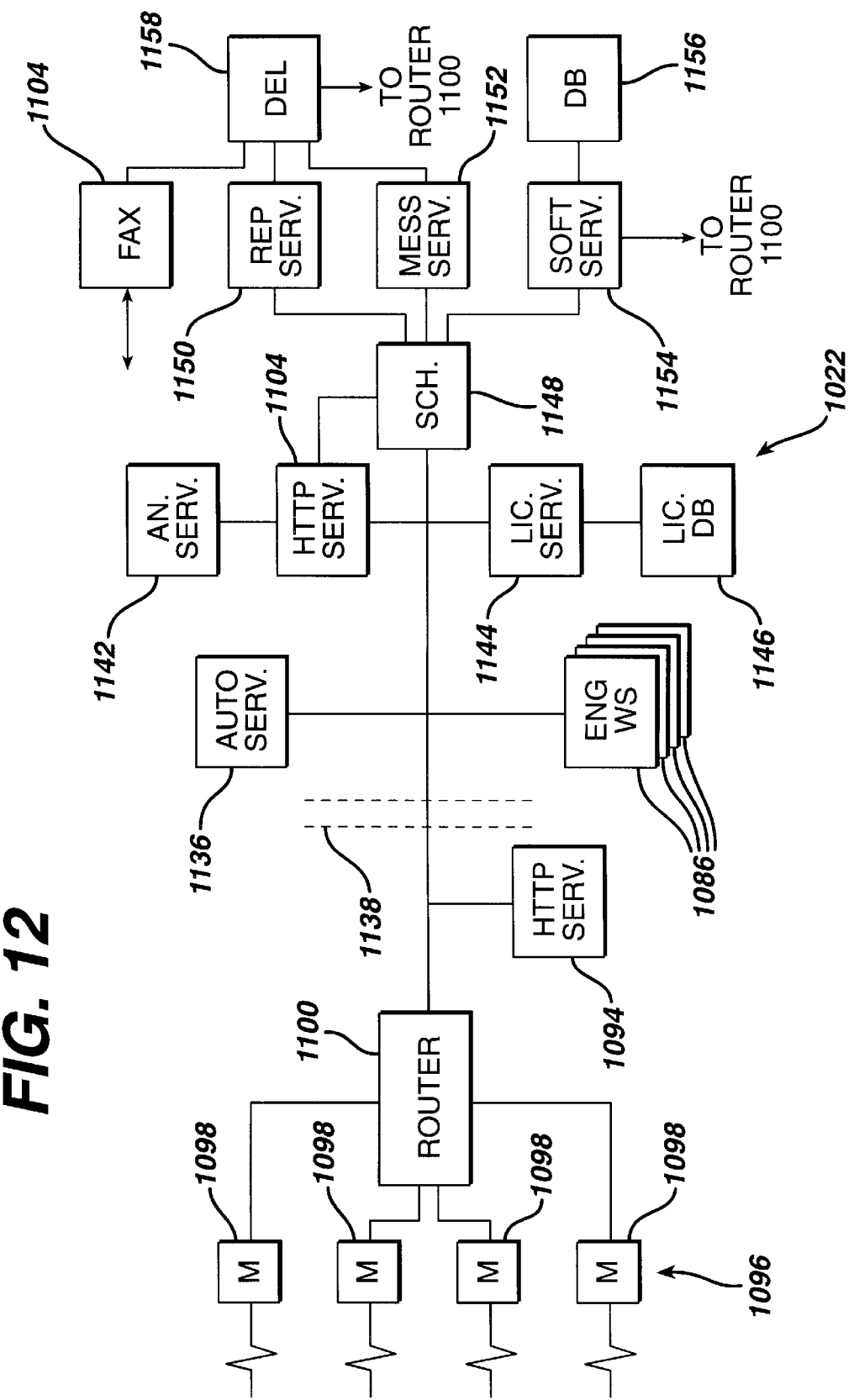
FIG. 12 is a block diagram of certain of the functional components of the service facility illustrated in FIGS. 9 and 10 for rendering interactive remote service to a plurality of medical diagnostic systems.

FIG. 12 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. Operator workstations 1086 are coupled to the port manager for handling service requests and transmitting messages and reports in response to such requests.

An automated service unit 1136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 1084. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, where desired, license server 1144 may be placed outside of fire wall 1138 to verify subscription status prior to admission to the service facility.

Handling of service requests, messaging, and reporting is further coordinated by a scheduler module 1148 coupled to HTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 12, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and 1154 are further coupled, along with communications module 1104, to a delivery handling module 1158, which is configured to receive outgoing messages, insure proper connectivity with diagnostic systems, and coordinate transmission of the messages.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a mainframe computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Advantageously, service system 1010 (FIG. 9) provides remote services, such as, remote diagnostics, remote control, remote monitoring, remote file storage, and remote servicing. Advantageously, service system 1010 (FIG. 9) allows the diagnosis system 10 to locate any one of the diagnostic knowledge database 12, the training unit 14, and the diagnostic unit 16 in a remote facility, such as in the present instance, service facility 1022. As such, the diagnosis system 10 (FIG. 1) incorporated into service system 1010 (FIG. 9), includes the capability of quick diagnostic and service functions, as described herein, while avoiding the necessity of having local equipment, such as, the diagnostic knowledge database 12, the training unit 14, and the diagnostic unit 16. Such equipment may be located in at least one remote facility. Multiple diagnosis systems may then cooperate to share high capacity databases and high speed processing units for diagnostic and service functions.

It is therefore apparent that there has been provided in accordance with the present invention, a system and method for diagnosing and validating an imaging machine using waveform data that fully satisfy the aims and advantages and objectives hereinbefore set forth. The invention has been described with reference to several embodiments, however, it will be appreciated that variations and modifications can be effected by a person of ordinary skill in the art without departing from the scope of the invention.

What is claimed is:

1. A system for diagnosing a machine from a remote facility over a network, comprising:
    a diagnostic knowledge base containing a plurality of rules for diagnosing faults in a machine and a plurality of corrective actions for repairing the faults;
    a diagnostic fault detector for categorizing waveform data generated from the machine as normal and faulty data, wherein the machine is connected to the remote facility over the network;
    a diagnostic feature extractor for extracting a plurality of features from the waveform data categorized as faulty data; and
    a diagnostic fault isolator coupled to the diagnostic feature extractor and the diagnostic knowledge base for isolating a candidate set of faults for the extracted features and identifying root causes most likely responsible for the candidate set of faults.

2. The system according to claim 1, wherein the waveform data comprises a plurality of time series plots.

3. The system according to claim 1, wherein the diagnostic fault detector comprises a gross filter and a fine filter.

4. The system according to claim 1, wherein the diagnostic feature extractor uses a time domain analysis, a frequency domain analysis, and a wavelet analysis.

5. The system according to claim 1, wherein the diagnostic fault isolator is a rule-based reasoning expert system.

6. The system according to claim 1, wherein the diagnostic fault isolator further comprises means for assigning a measure of confidence to each of the identified candidate set of faults, each measure of confidence indicating a belief that the fault is the most likely cause thereof.

7. The system according to claim 1, further comprising a diagnostic parser for removing extraneous data from the waveform data.

8. The system according to claim 1, further comprising a training unit coupled to the diagnostic knowledge base, the training unit comprising:
    means for obtaining a plurality of sets of waveform data taken from a plurality of machines connected to the remote facility over the network, each of the sets of waveform data having known faults associated therewith and a corresponding corrective action for repairing the faults;
    a training filter for categorizing each of the sets of waveform data as normal and faulty data;
    a training feature extractor for extracting a plurality of features from each of the sets of waveform data categorized as faulty data; and
    a training fault classifier for developing a plurality of rules that classify the feature extractions into a fault characterization and providing the plurality of rules to the diagnostic knowledge base.

9. The system according to claim 8, wherein the plurality of sets of waveform data comprise a plurality of time series plots.

10. The system according to claim 8, wherein the training filter comprises a gross filter and a fine filter.

11. The system according to claim 8, wherein the training feature extractor uses a time domain analysis, a frequency domain analysis, and a wavelet analysis.

12. The system according to claim 8, wherein the training fault classifier is a rule-based reasoning expert system.

13. The system according to claim 8, wherein the training unit further comprises a training parser for removing extraneous data from each of the sets of waveform data.

14. A method for diagnosing a machine having an unknown fault from a remote facility over a network, comprising the steps of:
    obtaining a plurality of rules for diagnosing faults and a plurality of corrective actions for repairing the faults;
    receiving new waveform data from the machine via the network;
    categorizing the new waveform data as normal and faulty data;
    extracting a plurality of features from the new waveform data categorized as faulty data; and
    isolating a candidate set of faults for the extracted features and identifying root causes most likely responsible for the candidate set of faults.

15. The method according to claim 14, wherein the new waveform data comprises a plurality of time series plots.

16. The method according to claim 14, wherein the step of categorizing the new waveform data as normal and faulty data comprises using a gross filter and a fine filter.

17. The method according to claim 14, wherein the step of extracting a plurality of features comprises using a time domain analysis, a frequency domain analysis, and a wavelet analysis.

18. The method according to claim 14, wherein the step of isolating a candidate set of faults and identifying root causes comprises using a rule-based reasoning expert system.

19. The method according to claim 14, further comprising the step of assigning a measure of confidence to each of the identified candidate set of faults, each measure of confidence indicating a belief that the fault is the most likely cause thereof.

20. The method according to claim 14, further comprising the step of removing extraneous data from the new waveform data.

21. The method according to claim 14, wherein the step of obtaining the plurality of rules for diagnosing faults and the plurality of corrective actions for repairing the faults comprises the steps of:

obtaining a plurality of sets of waveform data taken from a plurality of machines via the network, each of the sets of waveform data having known faults associated therewith;

categorizing each of the sets of waveform data as normal and faulty data;

extracting a plurality of features from each of the sets of waveform data categorized as faulty data; and developing a plurality of rules that classify the feature extractions into a fault characterization.

22. The method according to claim 21, wherein the plurality of sets of waveform data comprise a plurality of time series plots.

23. The method according to claim 21, wherein the step of categorizing each of the sets of waveform data as normal and faulty data comprises using a gross filter and a fine filter.

24. The method according to claim 21, wherein the step of extracting a plurality of features from each of the sets of waveform data comprises using a time domain analysis, a frequency domain analysis, and a wavelet analysis.

25. The method according to claim 21, further comprising the step of removing extraneous data from each of the sets of waveform data.

26. A system for performing a validation of waveform data generated from a machine, from a remote facility over a network, comprising:

a diagnostic knowledge base containing a plurality of rules for diagnosing faults in the machine;

a diagnostic fault detector, for categorizing the waveform data as normal and faulty data; and a diagnostic feature extractor for extracting a plurality of features from the waveform data categorized as normal data.

27. The system according to claim 26, wherein the waveform data comprises a plurality of time series plots.

28. The system according to claim 26, wherein the diagnostic fault detector comprises a gross filter and a fine filter.

29. The system according to claim 26, wherein the diagnostic feature extractor uses a time domain analysis, a frequency domain analysis, and a wavelet analysis.

30. The system according to claim 26, further comprising a diagnostic parser for removing extraneous data from the waveform data.

31. A method for performing a validation of waveform data generated from a machine, from a remote facility over a network, comprising the steps of:

obtaining a plurality of rules for diagnosing faults;

receiving new waveform data from the machine via the network;

categorizing the new waveform data as normal and faulty data with the plurality of rules; and extracting a plurality of features from the new waveform data categorized as normal data.

32. The method according to claim 31, wherein the new waveform data comprises a plurality of time series plots.

33. The method according to claim 31, wherein the step of categorizing the new waveform data as normal and faulty data comprises using a gross filter and a fine filter.

34. The method according to claim 31, wherein the step of extracting a plurality of features comprises using a time domain analysis, a frequency domain analysis, and a wavelet analysis.

35. The method according to claim 31, further comprising the step of removing extraneous data from the new waveform data.

* * * * *